(12) United States Patent
Hacikyan

(10) Patent No.: US 10,371,679 B2
(45) Date of Patent: Aug. 6, 2019

(54) WIRELESS OXYGEN MONITOR

(71) Applicant: Michael Hacikyan, Naples, FL (US)

(72) Inventor: Michael Hacikyan, Naples, FL (US)

(*) Notice: Subject to any disclaimer, the term of this patent is extended or adjusted under 35 U.S.C. 154(b) by 253 days.

(21) Appl. No.: 15/346,171

(22) Filed: Nov. 8, 2016

(65) Prior Publication Data

US 2018/0128799 A1    May 10, 2018

(51) Int. Cl.
   *G01N 33/00* (2006.01)
   *G01N 27/416* (2006.01)
   *B23K 9/32* (2006.01)
   *B23K 101/06* (2006.01)

(52) U.S. Cl.
   CPC ........... *G01N 33/0036* (2013.01); *B23K 9/32* (2013.01); *B23K 9/326* (2013.01); *G01N 27/4162* (2013.01); *B23K 2101/06* (2018.08)

(58) Field of Classification Search
   CPC ... G01N 33/0036; G01N 27/4162; B23K 9/16
   USPC ....................................................... 73/31.03
   See application file for complete search history.

(56) References Cited

U.S. PATENT DOCUMENTS

| | | | |
|---|---|---|---|
| 5,187,343 A * | 2/1993 | Edwards | B23K 9/325 138/90 |
| 5,479,359 A | 12/1995 | Rogero et al. | |
| 6,167,766 B1 | 1/2001 | Dunn et al. | |
| 2002/0009119 A1 | 1/2002 | Matthew et al. | |
| 2003/0173205 A1 | 9/2003 | Karlsson et al. | |
| 2004/0062684 A1 * | 4/2004 | McGee | G01N 33/84 422/68.1 |
| 2007/0035255 A1 | 2/2007 | Shuster et al. | |
| 2007/0107594 A1 | 3/2007 | Piccinni et al. | |
| 2012/0191349 A1 * | 7/2012 | Lenz | G01N 33/0075 702/2 |
| 2013/0244336 A1 | 9/2013 | Mayer et al. | |
| 2013/0284297 A1 * | 10/2013 | Hacikyan | F16L 55/134 138/93 |
| 2014/0102175 A1 * | 4/2014 | Wasden | G01K 13/02 73/29.02 |
| 2015/0076129 A1 | 3/2015 | Spear | |
| 2015/0273607 A1 | 10/2015 | Denis et al. | |
| 2016/0061799 A1 * | 3/2016 | Epperson | G01K 13/02 702/50 |
| 2016/0069833 A1 * | 3/2016 | Hacikyan | G01N 33/00 73/31.01 |
| 2016/0101481 A1 * | 4/2016 | Holverson | B23K 9/095 219/602 |

(Continued)

FOREIGN PATENT DOCUMENTS

GB    2457053 A  *  8/2009  .......... C05F 17/0282

OTHER PUBLICATIONS

Neutronics Inc., "Model OA-1S+ Portable Ultra-Trace Oxygen Analyzer Operations Manual", Oct. 2004, 29 pages.

(Continued)

*Primary Examiner* — Marrit Eyassu
(74) *Attorney, Agent, or Firm* — Walter W. Duft

(57) ABSTRACT

A wireless oxygen monitor for monitoring oxygen in a weld zone. The oxygen monitor receives weld zone gas samples and an oxygen sensor detects oxygen levels. A controller generates gas sample oxygen level data and wirelessly transmits gas sample data via an oxygen monitor wireless communication interface to a remote device that displays the gas sample data and logs it in a remote device storage.

17 Claims, 6 Drawing Sheets

(56) References Cited

U.S. PATENT DOCUMENTS

2016/0221107 A1* 8/2016 Kadlec .................... B23K 9/16

OTHER PUBLICATIONS

Neutronics Inc., "Model N2 Operations Manual", Oct. 2006, 28 pages.
Neutronics Inc., "Model 7100P Portable Oxygen Analyzer—Trace Range Operations Manual", Jan. 2001, 58 pages.
Huntingdon Fusion Techniques, "Argweld Purgeye 300 Weld Purge Monitor", Sep. 2013, 2 pages.
Huntingdon Fusion Techniques, "Argweld Purgeye 500 Weld Purge Monitor", Sep. 2013, 2 pages.
Huntingdon Fusion Techniques, "Purgeye 600 Weld Purge Monitor", Sep. 2013, 2 pages.
Huntingdon Fusion Techniques, "Purgeye 100 Weld Purge Monitor", May 2013, 4 pages.
Prestige Industrial Pipework Equipment, "Handy Purge Pro 5", Dec. 2011, 1 page.
Prestige Industrial Pipework Equipment, "Pro Purge 1 Weld Purge Monitor", Apr. 2014, 1 page.
TVC Ltd, "ALX II Portable Arc Welding Data-Logger and Monitoring System", May 2013, 2 pages.
TVC Ltd, "ALX II RS Arc Welding Data-Logger and Monitoring System", Nov. 2010, 2 pages.
Advanced Instruments Inc., "GPR-1200 MS Portable ppm Oxygen Analyzer", Oct. 2009, 32 pages.
PCT International Searching Authority, "Notification of Transmittal of the International Search Report and the Written Opinion of the International Searching Authority, or the Declaration", Counterpart PCT Application No. PCT/US2017/052403 claiming priority to U.S. Appl. No. 15/346,171, dated Jan. 19, 2018, 19 pages.

* cited by examiner

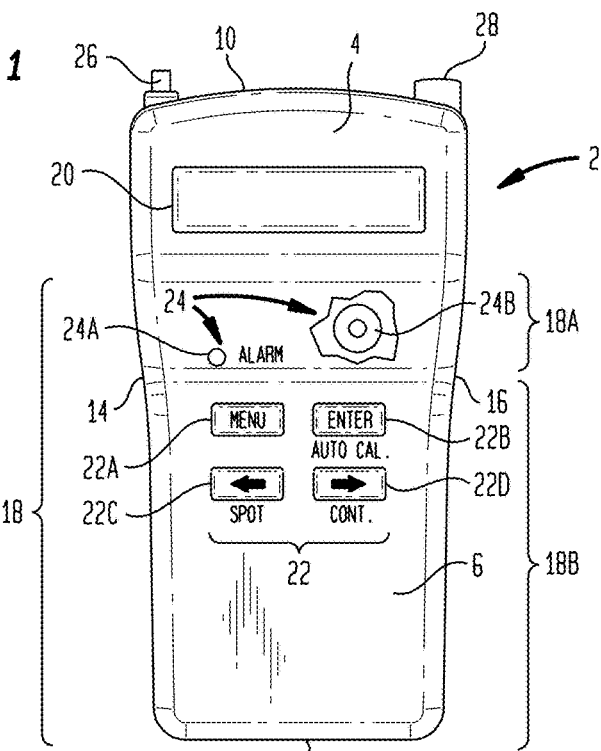
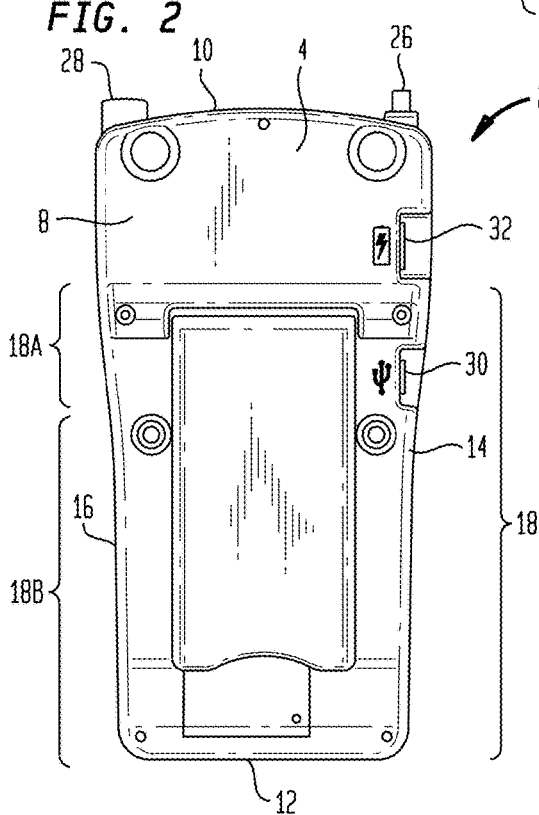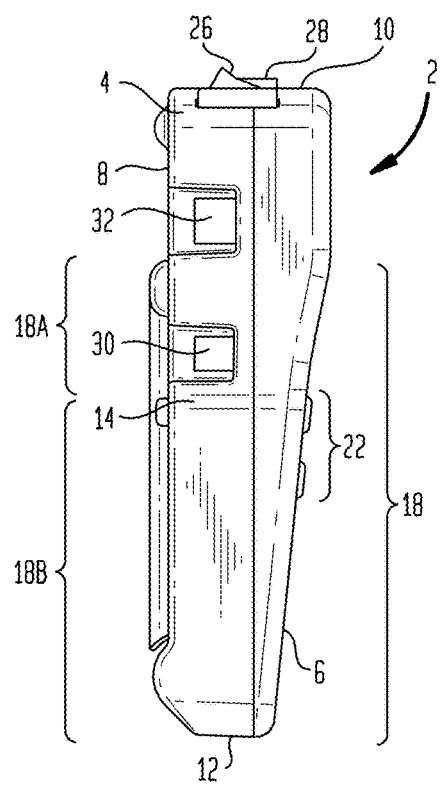

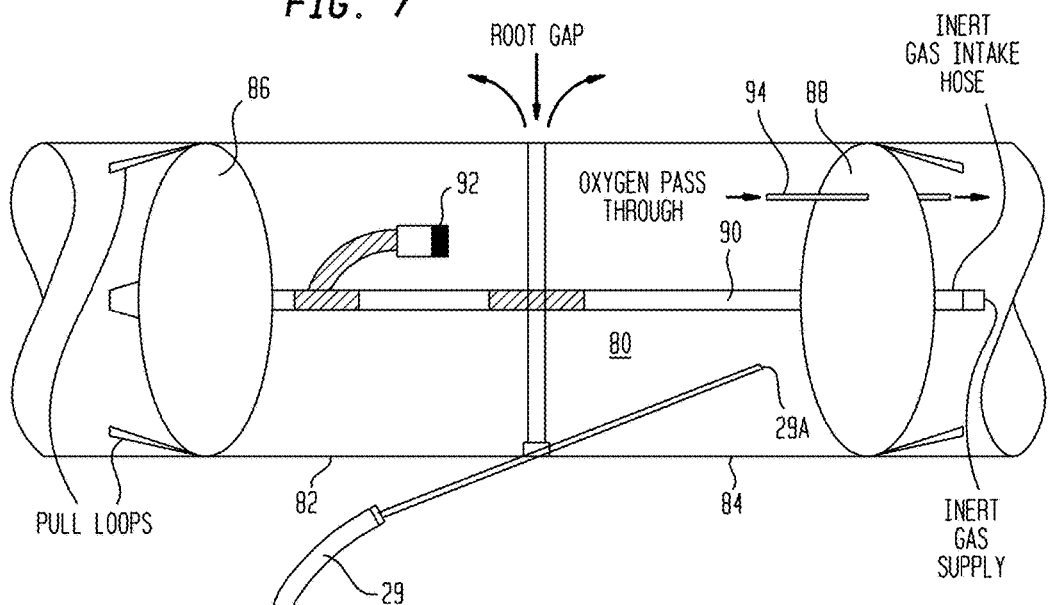
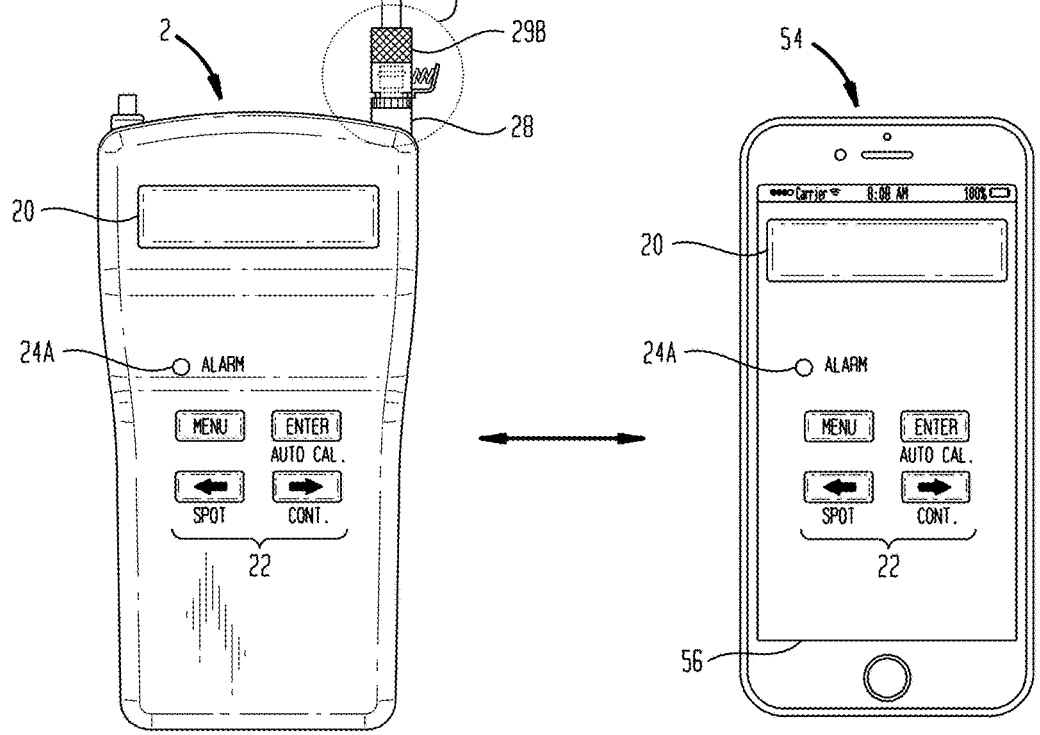
FIG. 7

WIRELESS OXYGEN MONITOR

BACKGROUND

1. Field

The present disclosure relates generally to inert gas welding. More particularly, the invention is directed to oxygen monitors for monitoring oxygen around a weld zone prior to and during an inert gas welding operation.

2. Description of the Prior Art

By way of background, inert gas welding is a species of arc welding in which the molten weld pool is shielded from atmospheric contamination and oxidation by bathing it with an inert gas, such as Argon, or a mixture of Helium and Argon. Popular examples of inert gas welding include TIG (Tungsten Inert Gas) welding and MIG (Metal Inert Gas) welding.

When welding together pipes and other enclosed structures using inert gas welding, it is important to purge the interior of the pipe or structure in the vicinity of the weld zone to prevent corrosion and the formation of oxides on the interior side of the weld pool. Purge dams are conventionally used for this purpose. For example, when butt-welding the ends of two pipe sections to form a consolidated pipe run, two purge dam structures are placed in the pipes, one in each pipe end on either side of the weld zone. A purge gas can then be introduced into the area between the dams to displace the oxygen therein.

It is common to use an oxygen monitor to determine whether sufficient oxygen removal has taken place for welding operations to proceed. Historically, such oxygen monitors have been non-portable apparatus of relative large size. More recently, portable hand-held oxygen monitors have become available. Although the portability of such devices enhances ease of use, hand-held oxygen monitors typically lack one or more features, which limits their usability in the field.

Today's oxygen monitors, portable or otherwise, require pipe purging personnel to periodically check a monitor display readout during initial purging to determine when the oxygen level has fallen to a level that is suitable for welding. The initial purge process may take anywhere from ten minutes to several hours, depending on pipe diameter and other factors. Periodically checking the oxygen monitor disrupts other tasks that pipe purging personnel may be performing while waiting for initial purging to complete. Although the portable oxygen monitor may be equipped with an audible alarm to signal when the oxygen level has fallen to a predetermined level, the pipe purging personnel may not be close enough to hear it.

Many oxygen monitors, particularly those of the portable variety, have a relatively small memory size that limits the number of gas sample data points that can be stored. Capturing gas sample data during welding is important because it facilitates future forensic analysis in the event of a weld failure. A welding operation may take anywhere from ten minutes to one hour, depending on pipe diameter and other factors. If gas sample data points are stored at relatively short time intervals, the welding time may be long enough to overflow an oxygen monitor's memory. This may result in old gas sample data points being overwritten by newer gas sample data points, and thereby lost. This problem can be mitigated somewhat by increasing the gas sample data point storage interval. However, doing so decreases logging granularity and may thereby reduce the accuracy of forensic analysis.

It is to improvements in the design and operation of portable oxygen monitors that the present disclosure is directed.

SUMMARY

A wireless oxygen monitor for monitoring oxygen in a weld zone is disclosed.

In an embodiment, a gas inlet port is operable to connect the oxygen monitor to a gas sampling probe.

In an embodiment, an electrochemical oxygen sensor is operable to receive gas samples from the gas inlet port, detect oxygen in the gas, and generate oxygen sensor outputs indicative of oxygen levels in the gas samples.

In an embodiment, a pump has a pump inlet in fluid communication with the inlet gas port and a pump outlet in fluid communication with the oxygen sensor.

In an embodiment, an oxygen monitor wireless communication interface is provided.

In an embodiment, an oxygen monitor storage is provided.

In an embodiment, an oxygen monitor controller is provided, and may be programmed to perform oxygen monitor operations.

In an embodiment, the oxygen monitor operations may include (1) activating the pump to draw gas samples from the gas inlet port and deliver the samples to the oxygen sensor, (2) receiving the oxygen sensor outputs from the oxygen sensor, (3) determining oxygen levels of the gas samples from the oxygen sensor outputs, and (4) wirelessly transmitting gas sample data via the wireless communication interface to a remote device that is operable to display the gas sample data on a remote device display and to perform remote device logging to log the gas sample data in a remote device storage.

In another aspect, distributed oxygen monitor system is provided that may include the above-summarized oxygen monitor and remote device.

In another aspect, a method is provided that may include using the above-summarized oxygen monitor and remote device to monitor oxygen in a weld zone established between two pipes to be welded together using an inert gas welding operation.

BRIEF DESCRIPTION OF THE DRAWINGS

The foregoing and other features and advantages will be apparent from the following more particular description of example embodiments, as illustrated in the accompanying Drawings, in which:

FIG. 1 is a front elevation view showing a portable hand-held oxygen monitor that may be constructed in accordance with the present disclosure, with a small section broken away to illustrate an audio output device within the monitor's housing;

FIG. 2 is a rear elevation view of the portable hand-held oxygen monitor of FIG. 1;

FIG. 3 is a side elevation view of the portable hand-held oxygen monitor of FIG. 1;

FIG. 7 is a diagrammatic view showing the portable hand-held oxygen monitor of FIG. 1 being used to monitor oxygen in a weld zone during a pipe-welding purge operation, and in wireless communication with a remote device that implements a remote device display to provide a user interface that mirrors the user interface of the portable hand-held oxygen monitor;

DETAILED DESCRIPTION OF EXAMPLE EMBODIMENTS

Figure 4:
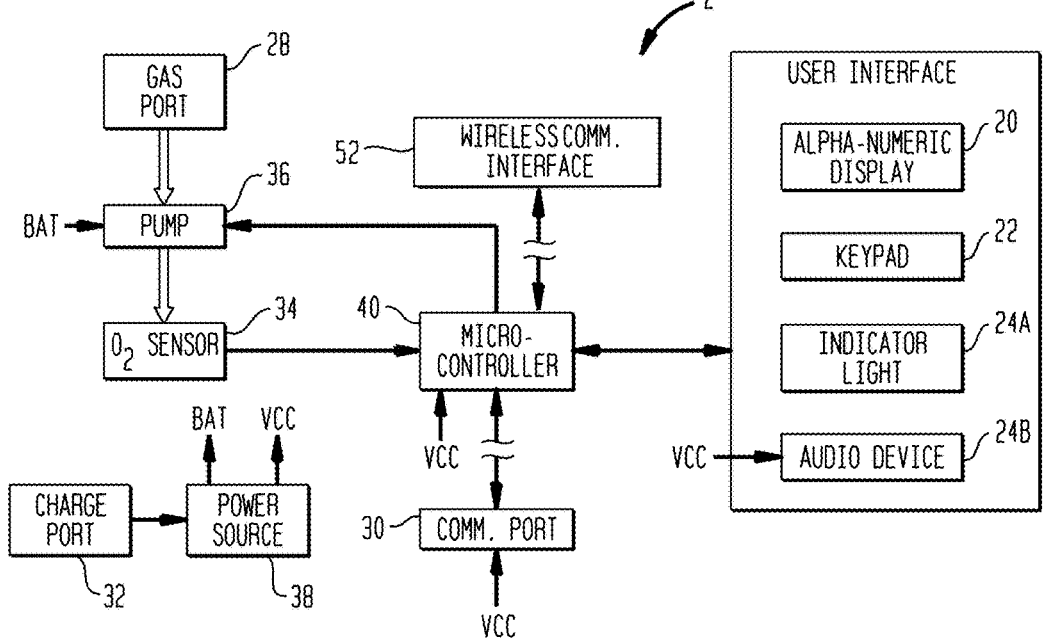
FIG. 4 is a functional block diagram showing example components of the portable hand-held oxygen monitor of FIG. 1.

Turning now to the drawing figures, which are not necessarily to scale, like reference numbers are used to represent like elements in all of the several views. FIGS. 1-3 illustrate a wireless oxygen monitor 2 representing an example oxygen monitor embodiment that may be constructed in accordance with the present disclosure. By way of example only, the oxygen monitor 2 may be constructed as a handheld portable device particularly suited for in-the-field use. For such applications, it may be necessary to monitor oxygen in a weld zone prior to and during a welding operation performed at a remote location (e.g., as opposed to in a welding shop). The oxygen monitor 2 includes a monitor housing 4 having a front 6, a back 8, a top 10, a bottom 12, and two sides 14 and 16 extending between the front and back and the top and bottom. The housing 4 has a hand-holding portion 18 that is sized and configured to be held in the palm of a monitor user's hand, with the user's thumb engaging one of the sides (14 or 16) and the user's remaining fingers engaging the other of the sides (14 or 16).

A user interface on the front of the housing includes an alphanumeric display 20 and one or more user interface buttons 22. By way of example only, the alphanumeric display 20 may comprise an LCD (liquid crystal display) element, and more preferably an LED (light-emitting diode) backlit LCD element. Using a backlit LCD element allows the displayed information to be easily discerned in outdoor sunlit conditions. By way of example only, the one or more user interface buttons 22 may comprise four user interface buttons 22A, 22B, 22C and 22D are shown in FIG. 1.

The user interface button 22A is labeled "MENU." Its function is to invoke a menu mode of the oxygen monitor 2. Example menu options that may be offered in this mode are described in more detail below.

The user interface button 22B is labeled "ENTER" and sub-labeled with the abbreviated words "AUTO CAL." This button performs both menu mode and non-menu mode functions. The menu mode function is to select a menu option displayed on the alphanumeric display 20. The non-menu mode function is to initiate an automatic calibration operation. As described in more detail below, this operation involves the oxygen monitor 2 obtaining an ambient air sample and evaluating its oxygen content for calibration purposes.

The user interface button 22C is labeled with a left-pointing arrow, and is sub-labeled with the word "SPOT." This button performs both menu mode and non-menu mode functions. The menu mode function is to navigate through the menu mode options in a first direction. The non-menu mode function is to initiate a spot gas sampling operation. As described in more detail below, this operation involves the oxygen monitor 2 obtaining and evaluating a single weld zone gas sample.

The user interface button 22D is labeled with a right-pointing arrow, and is sub-labeled with the abbreviated word "CONT." This button performs both menu mode and non-menu mode functions. The menu mode function is to navigate through the menu mode options in a second direction. The non-menu mode function is to initiate a continuous weld zone gas sampling operation. As described in more detail below, this operation involves the oxygen monitor 2 periodically obtaining and evaluating gas samples on a continuous basis until sampling is stopped by the monitor user.

An audiovisual alarm 24 may also be provided as part of the user interface. The audiovisual alarm 24 includes a small circular (or other shape) indicator light 24A on the front 6 of the housing 4, and an audio output device 24B within the housing. Advantageously, the indicator light 24A may be separate and distinct from the alphanumeric display 18 (i.e., it is a separate element) in order to increase the effectiveness of the audiovisual alarm 22 and thereby simplify and enhance the monitor user's welding experience. The indicator light 24A may be positioned at any suitable location on the front 6 of the monitor housing 4. The word "ALARM" is placed next to the indicator light 24A to clearly identify it to the monitor user.

The oxygen monitor 2 further includes a power switch 26 on the housing 4, a gas port 28 on the housing operable to connect the oxygen monitor 2 to a gas sampling probe 29 (shown in FIG. 7), a digital wireline communication port 30 on the housing operable to connect the oxygen monitor to a separate computer (not shown) via a data cable (not shown), and a charge port 32 on the housing operable to connect the oxygen monitor 2 to a charging device (not shown).

If desired, the sides 14 and 16 of the housing 4 may be contoured such that the two sides are varyingly tapered along the length of the hand-holding portion 18. For example, as shown in FIGS. 1 and 2, the sides 14 and 16 may have a first relatively steep taper over a relatively short upper segment 18A of the hand-holding portion 18, and a second relatively shallow taper over a relatively long lower segment 18B of the hand-holding portion. With this configuration, the sides 14 and 16 of the housing over the length of the hand-holding portion 18 will tend to match the naturally tapering space between the human thumb and remaining figures of the monitor user's hand as it grasps the housing 4, thereby improving ergonomic comfort.

If desired, the front 6 of the housing 4 may also be contoured such that it is varyingly tapered along the length of the hand-holding portion 18. For example, as shown in FIG. 3, the front 6 may have a first relatively steep taper over the relatively short upper segment 18A of the hand-holding portion 18, and a second relatively shallow taper over the relatively long lower segment 18B of the hand-holding portion. With this configuration, the indicator light 24A of the audiovisual alarm 24, which is located on the relatively steeply tapered upper segment 18A, will be more prominently viewable and differentiable from the alphanumeric display 20, which is located above the hand-holding portion 18 of the housing 4. The user interface buttons 22 are located on the relatively shallowly tapered lower segment 18B. The shallow taper enhances the ergonomic presentation of these buttons to the monitor user.

Although varyingly tapered, the hand-holding portion 18 of the housing 4 will inherently have an average thickness dimension and an average width dimension. The average thickness dimension represents the average distance between the front 6 and back 8 of the housing 4 over the length of the hand-holding portion 18. The average width dimension represents the average distance between the two sides 14 and 16 of the housing 4 over the length of the hand-holding portion 18. In an example embodiment, the average thickness dimension is preferably less than or equal to the average width dimension to provide satisfactory ergonomic comfort. By way of example, the average thickness dimension may be approximately 1.5-2.5 inches, and the average width dimension may be approximately 2.5-3.5 inches.

Figure 5:
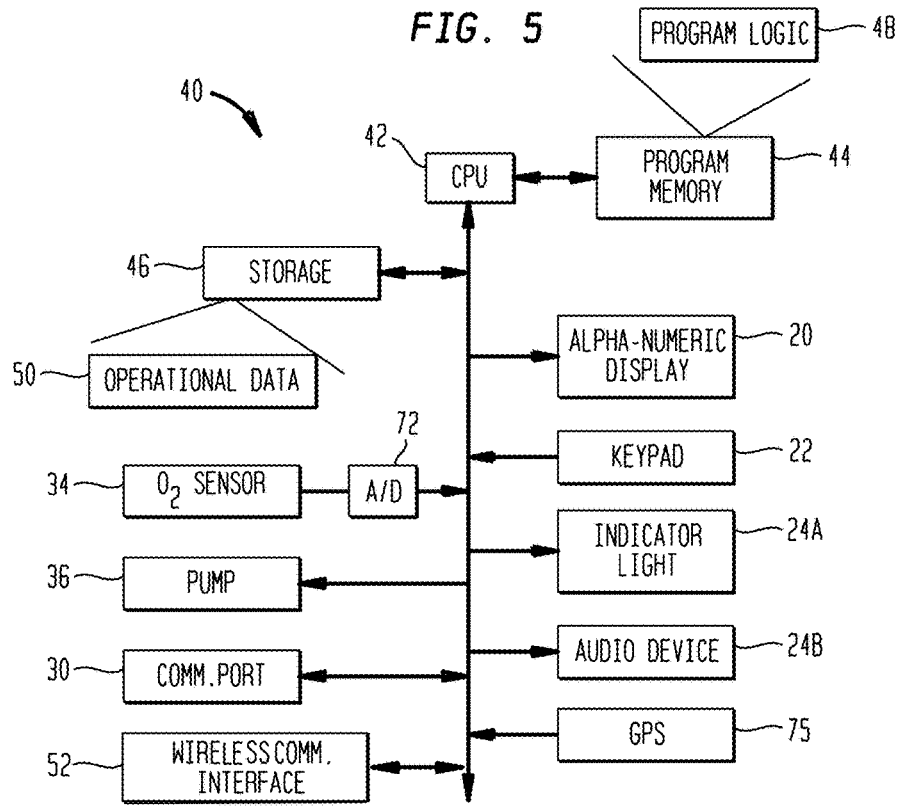
FIG. 5 is a functional block diagram showing an example microcontroller and its connections to other components of the portable hand-held oxygen monitor of FIG. 1.

With additional reference now to FIG. 4, within the housing 4 is an electrochemical oxygen sensor 34 and a pump 36 having a pump inlet in fluid communication with the gas port 28 and a pump outlet in fluid communication with the oxygen sensor. A direct current power source 38 is also provided within the housing 4, as is a controller of a type that is suitable for controlling oxygen monitor operations. As shown in FIG. 5, the controller may be implemented as a microcontroller 40. The microcontroller 40 may include a CPU (Central Processing Unit) 42 operably coupled to a non-volatile program memory module 44 (such as a flash program memory) via a memory bus, and to a non-volatile storage module 46 (such as a standard EEPROM) via a main bus. The program memory module 44 and the storage module 46 comprise non-transitory computer-readable storage media, and each represents a type of microcontroller "memory." The program memory module 44 may be used to store microcontroller program instructions and temporary (e.g., stack) data, identified in FIG. 5 as program logic 48. The storage module 46 may be used to store permanent data, including data generated during oxygen monitor operations, identified in FIG. 5 as operational data 50. The microcontroller 40 is further operably coupled to the user interface components 20, 22, 24A and 24B, the digital communication port 30 (via a communications protocol controller (not shown)), the oxygen sensor 34, the pump 36 and the direct current power source 38. The direct current power source 38 is operable via the power switch 26 and connected to provide electrical power to various monitor components, and to receive electrical power from the charge port 32. In an example embodiment, the power source 38 may be implemented as a rechargeable battery.

As further shown in FIGS. 4 and 5, the oxygen monitor 2 includes a wireless communication interface 52 operably coupled to the microcontroller 40. The wireless communication interface 52 supports wireless communication between the oxygen monitor 2 and a remote device 54, as shown by way of example in FIGS. 7-9. The wireless communication interface 52 may be implemented in various ways, including as a wireless network interface adapted for use in a Personal Area Network (PAN), a Local Area Network (LAN), a Wide Area Network (WAN), a cellular network, etc. Such networks support wireless communication over various ranges, from 10s of meters to unlimited world-wide coverage via the Internet.

If the wireless communication interface 52 is implemented as a wireless PAN network interface, it may be configured to support any of a variety of wireless PAN interface protocols. One such protocol would be the Bluetooth® protocol outlined in the IEEE 802.15 family of specifications and currently managed by the Bluetooth Special Interest Group (SIG). In an embodiment, a Class 2 Bluetooth implementation of the wireless communication interface 52 may be adapted for short range communication within a range up to approximately 30 meters. In another embodiment, a Class 1 Bluetooth implementation of the wireless communication interface 52 may be adapted for short range communication within a range up to approximately 100 meters.

Figure 6:
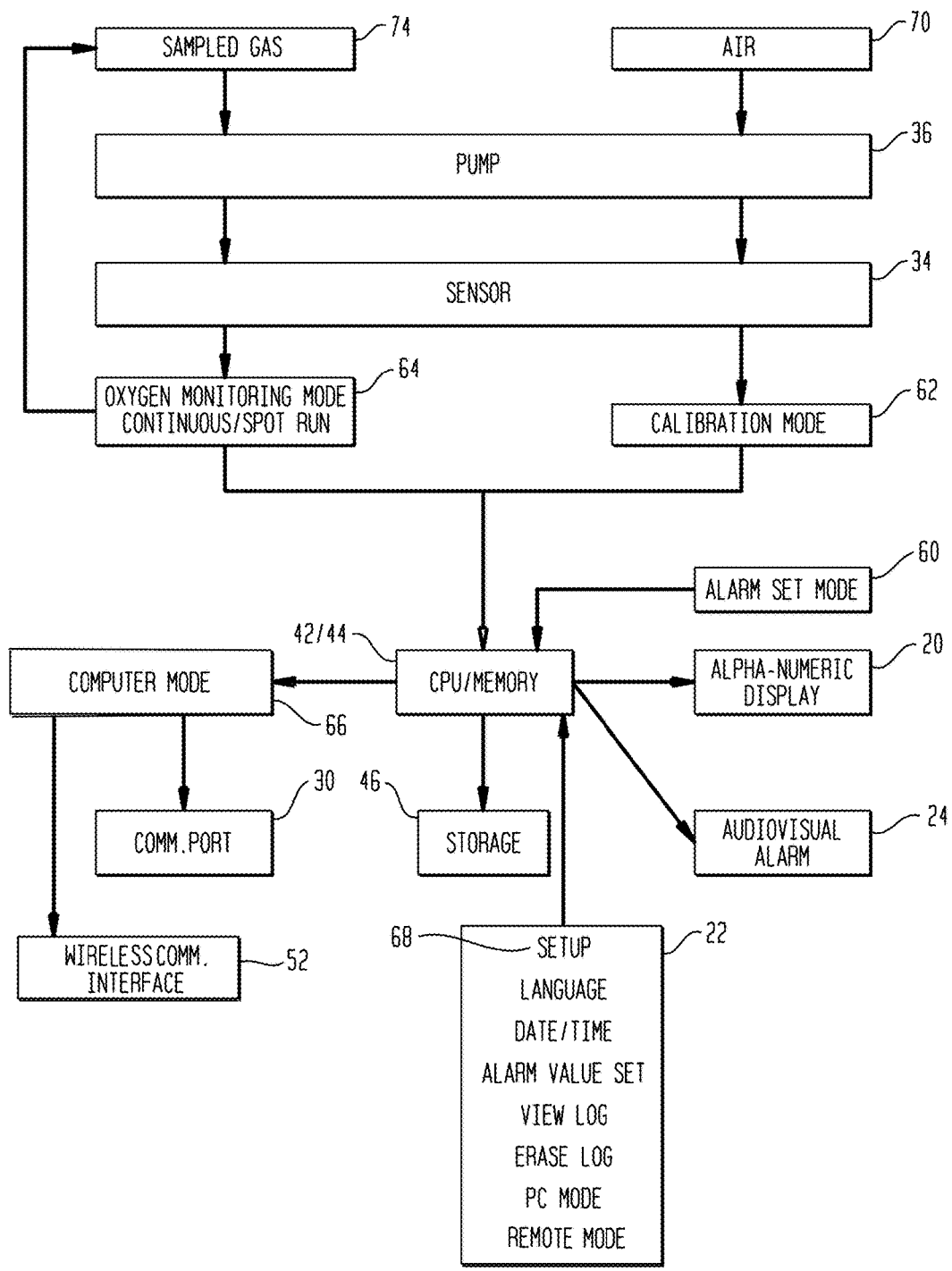
FIG. 6 is a functional block diagram showing example functions (and components) of the portable hand-held oxygen monitor of FIG. 1.

The programming instructions comprising the program logic 48 are used to program the microcontroller's CPU 42 to perform various functions and operations. As shown in FIG. 6, these functions and operations may include an alarm set mode 60, an automatic calibration mode 62, an oxygen monitoring mode 64, and a computer mode 66. Each of these operational modes is implemented by the microcontroller 40 in response to activation of one or more of the user interface buttons 22. Example embodiments of these operational modes are described in more detail hereinafter.

Two of the operational modes, namely, the alarm set mode 60 and the computer mode 66, are invoked via the MENU button 22A. Thus, it is appropriate to briefly discuss the various menu options that this button may be configured to provide. In the embodiment of FIGS. 1-6, the MENU button 22A is used to display a SETUP menu 68 (see FIG. 6) on the alphanumeric display 20. In an embodiment, only one menu option is displayed at a time. Desired options are reached using the buttons 22C and 22D to scroll through the selections, and then pressing the ENTER button 22B to select the option of interest. The first three options are a LANGUAGE setup option for selecting a desired display language, a DATE/TIME setup option for inputting the date and time of a particular welding job, and an ALARM VALUE SET option for invoking the alarm set mode 60. These first three options are for use prior to the oxygen monitor 2 being operated for purging. Note that in addition to allowing a monitor user to store date and time information for a particular welding job, one or more additional SETUP menu options could be added to allow a monitor user to store additional job information, such as weld site location in case the welding log data stored by the oxygen monitor (see below) ever needs to be associated with a particular welding location on a pipeline or other structure (e.g. for forensic purposes). The second three options provided by the SETUP menu 68 are a VIEW LOG option for viewing log data concerning a welding job, an ERASE LOG option for erasing the log data, and a PC MODE option for invoking the computer mode 66 in order to upload the log data to a separate computer. The final option is the REMOTE MODE option for invoking the computer mode 66 in order to establish wireless communication with the remote device 54 via the wireless communication interface 52, transfer gas sample data to the remote device in real time, and optionally receive control inputs from the remote device. This functionality is described in more detail below.

The alarm set mode 60 allows a monitor user to specify an oxygen level that will trigger an alarm output from the audiovisual alarm 24 during the oxygen monitoring mode 64. As mentioned above, the program operations comprising the alarm set mode 60 are invoked using the MENU button 22A. This displays the SETUP menu 68 in the alphanumeric display 20. The monitor user presses either of buttons 22C or 22D to scroll through the menu selections until the ALARM VALUE SET option is reached, and then presses the ENTER button 22B. When the ALARM VALUE SET option is invoked, the microcontroller 40 presents a range of suggested oxygen level alarm values for selection by the monitor user via the user interface 22. By way of example, the oxygen level alarm values may be presented as a list that the monitor user can step through in a forward direction by pressing the arrow button 22D or in a reverse direction by pressing the arrow button 22C. When the desired oxygen level alarm value is reached, the monitor user presses the ENTER button 22B. This will cause the microcontroller 40 to receive the oxygen level alarm value as a user selection, and store it the microcontroller's memory, namely, as part of the operational data 50 in the storage module 46. As a further option, the oxygen monitor 2 could be configured so that the ALARM VALUE SET menu option allows a monitor user to disable the audiovisual alarm 24.

The program operations comprising the automatic calibration mode 62 are implemented (when the oxygen monitor is not in menu mode) in response to the monitor user pressing the AUTO CAL. button 22B. As shown in FIG. 6, when the automatic calibration mode 52 is invoked, the microcontroller 40 activates the pump 36 to draw an ambient air sample 70 from the probe attached to the gas port 28, and deliver the sample to the oxygen sensor 34. The oxygen sensor 34 detects the amount of oxygen in the ambient air sample 70, and outputs a corresponding analog voltage. The oxygen sensor's analog voltage output is input to an A/D (Analog/Digital) converter 72 (see FIG. 5) that may be integrated with the microcontroller 40, and which converts the analog voltage to a digital ambient oxygen level value. The ambient oxygen level value is stored as part of the operational data 50 in the microcontroller's memory, namely, in the storage module 46.

In an example embodiment, the storage module 46 also stores an ambient air calibration percentage value representing a known oxygen content percentage for air. For example, at sea level, the oxygen content of air, by volume, is 20.946%. This default percentage value may be placed in the storage module 46 as a factory setting of the oxygen monitor 2. It need not be set by the monitor user. By knowing both the oxygen content of air as a percentage value and the ambient oxygen level value determined during automatic calibration, the microcontroller 40 can determine the oxygen content of a gas sample obtained during welding and display it as a percentage value. This is described in more detail below in the discussion of the oxygen monitoring mode 64. As also described below, the oxygen content of a gas sample obtained during welding could be additionally displayed in parts per million by volume (ppm). This may be done using a stored ambient air calibration ppm value representing a known oxygen ppm for air. Or, the ambient air calibration ppm value may be easily computed from the ambient air calibration percentage value. For example, given that the oxygen content in air is 20.946% by volume, its ppm would be 0.20946×1 million=209,460 ppm. It would also be possible to store the ambient air calibration ppm value and compute the ambient air calibration percentage value therefrom. Once automatic calibration is done, the monitor user can operate the oxygen monitor 2 to measure the oxygen level in a welding purge zone prior to and during a welding operation.

The program operations comprising the oxygen monitoring mode 64 are implemented (when the oxygen monitor is not in menu mode) in response to the monitor user pressing either the SPOT button 22C or the CONT. button 22D. The SPOT button 22C invokes spot monitoring to obtain a single oxygen reading whereas the CONT. button 22D invokes continuous monitoring to obtain plural periodic oxygen readings. As shown in FIG. 6, when either button is pressed, the microcontroller 40 activates the pump 36 to draw a sample of the unknown gas 74 from the probe attached to the gas port, and deliver it to the oxygen sensor 34. The oxygen sensor 34 detects the amount of oxygen in the gas sample 74 and outputs a corresponding analog voltage that is converted by the A/D converter 72 to a digital gas sample oxygen level value. The microcontroller 40 then compares the gas sample oxygen level value to the oxygen level alarm value previously stored in the memory, and may activate the audiovisual alarm 24 if the gas sample oxygen level value is equal to or less than the oxygen level alarm value. This activating may include illuminating the indicator light and generating a sound from the audio output device to alert a monitor user that is safe to weld. In an embodiment, the microcontroller 40 may repetitively activate then deactivate the indicator light and the audio output device in synchronization with each other in order to increase the effectiveness of the alert by making it more distinct.

In an embodiment, the oxygen monitoring mode 64 may further include the microcontroller 40 outputting the gas sample oxygen level value to the alphanumeric display 20, and the alphanumeric display displaying the value in alphanumeric form. The gas sample oxygen level value may be displayed as an oxygen level percentage value (by volume), an oxygen level ppm value, or both. Displaying both oxygen level formats may be advantageous because some monitor users are used to working with oxygen percentage values while others are used to working with ppm values. In an embodiment, a menu option could be provided for selectively displaying oxygen percentage values and/or ppm values.

Determining an oxygen percentage value can be handled using the gas sample oxygen level value in conjunction with the ambient oxygen level value and the ambient air calibration percentage value described above. In particular, the oxygen percentage of the gas sample 74 can be determined by Equation (1) below:

gas sample oxygen level percentage value=(ambient air calibration percentage value)×(gas sample oxygen level value/ambient oxygen level value).    Equation (1):

Similarly, determining an oxygen ppm value can be handled using the gas sample oxygen level value in conjunction with the ambient oxygen level value and the ambient air calibration ppm value described above (which may be separately stored or derived on the fly from the ambient air calibration value. In particular, the oxygen level ppm of the gas sample 74 can be determined by Equation (2) below:

gas sample oxygen level ppm value=(ambient air calibration ppm value)×(gas sample oxygen level value/ambient oxygen level value).    Equation (2):

If the oxygen monitoring mode 64 is invoked by the SPOT button 22C to obtain a spot reading, the foregoing operations happen only once. If the oxygen monitoring mode 64 is invoked by the CONT. button 22D to obtain continuous readings, the foregoing operations are repeated periodically at predetermined intervals (e.g., every second) on a continuous basis, until the monitor user discontinues oxygen monitoring by pressing the CONT. button a second time.

In an embodiment, the oxygen monitoring mode 64 may include data logging in which the microcontroller stores logging event data as part of the operational data 50 in the microcontroller's memory, namely, in the storage module 46. Logging may be implemented automatically, with user control being limited to viewing log data via the VIEW LOG menu option or deleting it via the ERASE LOG menu option. Alternatively, the oxygen monitor 2 could be configured to allow the monitor user to enable or disable logging.

The logging event data may include, for each logging event, one or more gas sample oxygen level values obtained during the welding operation by the oxygen monitor 2. The one or more gas sample oxygen levels may be stored in association with timestamps indicating when the gas samples 74 were obtained. The oxygen level values may be stored in raw form, as oxygen level percentage values, as oxygen level ppm values, or any combination of the above. The logging event data may also indicate whether the audiovisual alarm 24 was activated at the time of the logging event. For spot oxygen monitoring, there will be a single logging event. For continuous oxygen monitoring, there will be several logging events. By way of example, a logging event could be performed for every "n" gas sample readings, where "n" is selected based on a desired logging event frequency taking into the account the limits on storage space available in the storage module 46. Thus, if gas sample readings are taken once per second, a logging event could be performed every 15 readings, representing a 15 second time span between logging events. The timestamp information stored in a logging event could include the DATE/TIME information entered via the SETUP menu 68. Additionally, the microcontroller 40 could generate individual timestamps each time a gas sample 74 is obtained. Other information stored via the SETUP menu in connection with a particular welding job could also be logged. By way of example, this could include weld location information, such as a location on a pipeline or other welded structure where a weld was made and the logging data was generated. One advantage of capturing such location information would be for forensic purposes in the event of a subsequent weld failure. Although not shown, an embodiment of the oxygen monitor 2 could include a locating device, such as a GPS (global positioning system) unit 75 (see FIG. 5), that can automatically generate the monitor location information for storage as part of the operational data 50 in the microcontroller's memory, namely, in the storage module 46. The automated location information could be stored as part of the logging data.

As mentioned above, the program operations comprising the computer mode 66 are invoked using the MENU button 22A. This displays the SETUP menu 68 in the alphanumeric display 20. The monitor user presses either of buttons 22C or 22D to scroll through the menu selections until the PC MODE option or the REMOTE MODE option is reached, and then presses the ENTER button 22B. When the PC MODE option is invoked, the microcontroller 40 establishes communication with a separate computer (not shown) connected to the communication port 30 via a cable, and uploads the logging event data from the microcontroller memory, namely the storage module 46, to the computer. When the REMOTE MODE option is invoked, the microcontroller 40 establishes communication with the remote device 54 via the wireless communication interface 52, and prepares the oxygen monitor 2 to transfer gas sample data to the remote device in real time, and optionally to receive control input from the remote device. This is described in more detail below in connection with FIG. 7.

Turning now to FIG. 7, the portable oxygen monitor 2 is shown as it monitors oxygen in a pipeline weld zone 80 during a weld zone purging operation. In FIG. 7, a pair of pipes 82/84 are to be butt-welded together at a welding root gap. A purge dam apparatus installed within the pipes has first and second pipe blocking members 86 and 88 that, for purposes of example only, may be implemented as inflatable purge bladders. The purge bladders 86 and 88 are joined together by an intermediate bridge conduit 90. FIG. 7 shows the purge dam apparatus after the purge bladders 86 and 88 have been inflated with an inert gas from an inert gas supply (not shown). The inert gas is fed from the inert gas supply through an inert gas intake hose connected to a port on the right-hand purge bladder 88. The inert gas inflates both purge bladders 86/88, and also flows into the weld zone 80 via a purge gas outlet port 92 connected to the bridge conduit 90. The enclosed space between the purge bladders represents the weld zone 80, which is purged of air by the purge gas following the introduction thereof through the purge gas outlet port 92. Oxygen displaced by the incoming purge gas exits the weld zone 80 via the root gap, and also through a vent port 94 extending through the right-hand purge bladder 88.

As can be seen, the oxygen monitor 2 is operable to obtain oxygen readings from the weld zone 80 using the detachable probe 29. A rigid probe tip 29A at the inlet end of the probe 29 is inserted into the root gap so that it can draw gas samples from the weld zone 90. The probe tip 29A can be made of steel or other material that can withstand the heat from the welding operation. Advantageously, the probe tip 29A is long so that it can collect gas samples from deep in the weld zone 80. Preferably, the probe tip 29A is at least approximately 100 mm long so that it can will reach the centerline of a pipe having a diameter of 200 mm. More preferably, the probe tip 29A will be longer so that it can probe the side regions of the weld zone 80, as shown in FIG. 7. In an example embodiment, the probe tip 29A is at least approximately 160 mm in length. The probe tip 29A is also as thin as possible while still being capable of drawing gas samples in order to minimize root gap width. Preferably, the outside diameter of the probe tip 29A will not exceed approximately 5 mm. In an example embodiment, the probe tip 29A has an outside diameter of not more than approximately 2 mm, with an inside diameter of approximately 1 mm. The base end of the probe tip has an enlarged fitting that mounts to one end of a flexible tube portion of the probe 29.

Figure 7A:
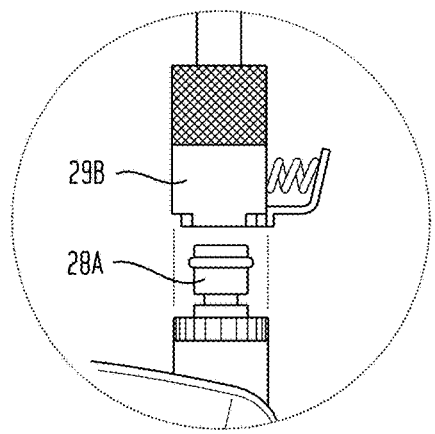
FIG. 7A is an inset view from FIG. 7 showing a quick-connect coupling between a gas port of the portable hand-held oxygen monitor of FIG. 1 and a gas-sampling probe.

As additionally shown in FIG. 7A, the outlet end of the probe 29 mounts a female quick-connect fitting 29B that is connected to a counterpart male quick-connect fitting 28A mounted on the gas port 28 on the oxygen monitor 2. The female quick-connect fitting 29B is provided with a spring-loaded disconnect push button clasp that lockingly engages a channel on the male quick-connect fitting 28A, such that the quick-connect fittings are hand-operable. A resilient O-ring is provided on the male quick-connect fitting 28A to ensure a high-quality pressure seal. The above-described style of hand-operable quick-connect coupling is conventionally used with low pressure tubing. Other types of hand-operable quick-connect couplings may also be used in lieu of the illustrated components.

The quick-connect fittings 28A and 29B interlock to form a gas-tight connection between the oxygen monitor 2 and the probe 29. This interlocked coupling arrangement prevents gas leakage, which has been known to occur in prior art oxygen monitors in which a threaded connection is used for the probe. In such prior art oxygen monitors, the monitor user may fail to fully thread the probe onto the monitor. Also, rotation of the oxygen monitor or the probe creates torque that can loosen the threaded connection, or twist and kink the probe's flexible tube, which can lead to false oxygen level readings. In the disclosed oxygen monitor 2, the quick-connect fitting 29B is free to swivel when interlocked with the quick-connect fitting 28A, thereby eliminating torque, and twisting and kinking of the probe tube.

During weld zone purging, the microcontroller 40 of the oxygen monitor 2 will activate the pump to draw one or more weld zone gas samples from the gas inlet port 28 and deliver the sample(s) to the oxygen sensor 34. As noted above, only one gas sample will be obtained for spot monitoring and multiple gas samples will be obtained for continuous monitoring. Analog outputs from the oxygen sensor 34 are converted to digital form by the A/D converter 72 (see FIG. 5) and received by the microcontroller 40. The microcontroller 40 processes the digitized oxygen sensor output(s) to determine the oxygen level of the gas sample(s). As previously noted, the gas sample oxygen level information is may be displayed on the alpha-numeric display 20. Moreover, once the oxygen level in the weld zone 80 has dropped to the oxygen level alarm value stored by the oxygen monitor 2, the audiovisual alarm 24 may activate, alerting the monitor user that welding may proceed.

If gas sample logging is being performed, the microcontroller 40 will periodically log gas sample data in the oxygen monitor storage 46, the gas sample data including the gas sample oxygen levels of some or all of the gas samples. Because the size of the oxygen monitor storage 46 may be quite limited (e.g., 1 megabyte or less) the oxygen monitor logging may entail writing a first set of gas sample data to the oxygen monitor storage 46 until the storage is full, then continuing to store additional gas sample data in the storage by overwriting storage locations that store the first set of gas sample data with a second set of gas sample data. This is a FIFO operation, with the older stored gas sample data being overwritten before newer data.

If the REMOTE MODE of operation is being utilized, the microcontroller 40 will wirelessly transmit the gas sample data via the wireless communication interface 52 to the remote device 54. The remote device 54 may be situated away from the weld zone 80 at some distance from the oxygen monitor 2, such as 30 meters, 100 meters, etc., up to and including world-wide coverage, depending on the nature of the wireless communication interface 52. By way of example only, the data transfer between the oxygen monitor 2 and the remote device 54 may utilize direct peer to peer communication. Alternatively, the data transfer may involve one or more intermediate devices, such as PAN, LAN, WAN or cellular network entities.

In the REMOTE MODE of operation, the oxygen monitor 2 and the remote device 54 will function as a distributed oxygen monitor system. In some cases, there may be more than one remote device 54, such as when different remote devices are used by different personnel involved in a single weld zone purging operation. In an embodiment, the remote device 54 displays the gas sample data on its own remote device display, and may also perform remote device logging to log the gas sample data in a remote device storage. The remote device 54 may be implemented in many different ways, including as a portable device such as a cellular telephone, tablet or laptop computer, or as a non-portable device such as a desktop computer.

Figure 8:
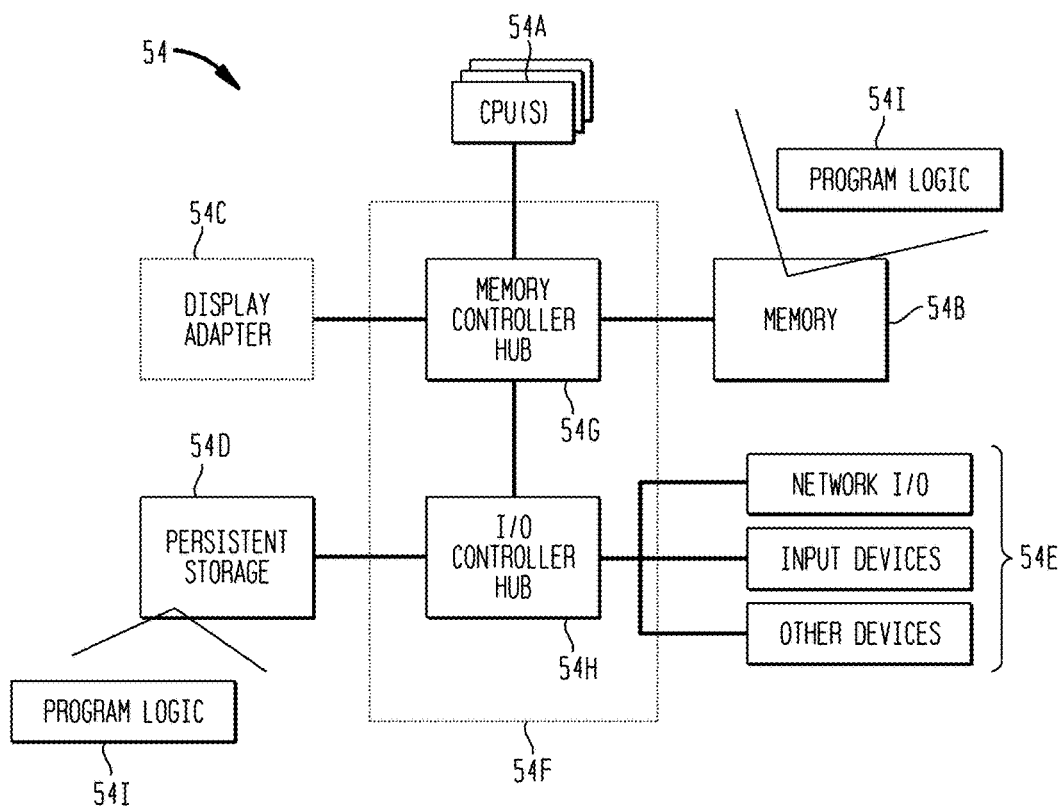
FIG. 8 is a functional block diagram illustrating example hardware and software components that may be used to implement the remote device of FIG. 7.

FIG. 8 illustrates example hardware components that may be used to implement the remote device 54. The hardware components of FIG. 8 include one or more CPUs or other logic-implementing hardware 54A that may operate in conjunction with a memory 54B (e.g., RAM, ROM, or a combination thereof) to provide a data processing core. A display adapter 54C generates visual output information (e.g., text and/or graphics) to an associated remote device display (e.g., the touch screen 56 of FIG. 7, described below). Additional components shown in FIG. 8 include a persistent data storage resource 54D (e.g., a disk drive, a solid state drive, flash storage, etc.) and various peripheral devices 54E. The peripheral devices 54E may include conventional I/O resources, such as a remote device wireless communication interface (Bluetooth®, Ethernet, WiFi, Cellular, etc.). The peripheral devices 54E may further include an input device such as a touch screen, a keyboard (real or virtual), and possibly a pointing device (in remote devices 54 that support such functionality). Other types of peripheral devices 54E may also be provided, as needed. A bus infrastructure 54F, which may include a memory controller hub or chip 54G (e.g., a northbridge) and an I/O (input/output) controller hub or chip 54H (e.g., a southbridge), may be used to interconnect the foregoing components. It should be understood that the above-described hardware components are set forth as examples only, and that other suitable hardware components and component arrangements may also be used to implement the remote device 54.

FIG. 8 additionally shows program logic 54I that may be permanently stored in the remote device storage resource 54D (or elsewhere) and loaded in the memory 54B during program execution. The program logic 54I controls the remote device 54 to perform various remote device operations. These operations may include, but are not limited to, wirelessly receiving gas sample data containing gas sample oxygen levels from the oxygen monitor 2, displaying the gas sample oxygen levels on the remote device display (e.g., touch screen 56), performing remote device logging to log the gas sample data in the remote device storage 54D, and remotely controlling oxygen monitor operations.

FIG. 7 illustrates an example remote device 54 implemented as a computerized cellular telephone (e.g., a smartphone). In this embodiment, the remote device display is provided by a cellular telephone touch screen 56. If desired, the touch screen 56 may be configured to display a mirror user interface that emulates some or all of the user interface elements provided on the front side of the oxygen monitor 2. The touch screen 56 may thus provide emulated versions of the oxygen monitor alpha-numeric display 20, the user interface buttons 22, and the alarm indicator light 24A. The oxygen monitor's audio output device 24B may be emulated by the cellular telephone's audio functionality.

Figure 9:
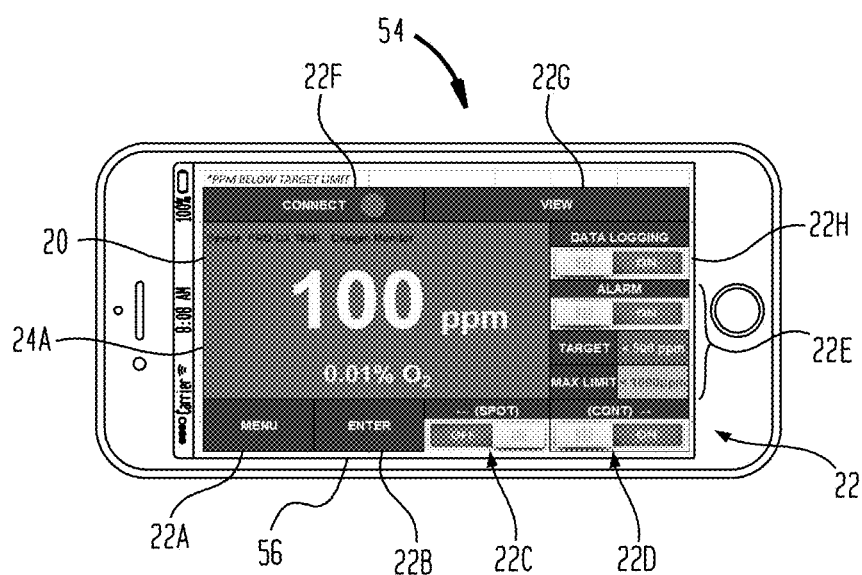
FIG. 9 is a diagrammatic view of the remote device of FIG. 7 in which the remote device display provides an alternative user interface.

In addition to (or in lieu of) emulating the oxygen monitor's user interface elements, various other remote device display configurations may be provided. FIG. 9 is illustrative. It depicts the touch screen 56 of the remote device 54 displaying a native user interface that may provide native remote device versions of the oxygen monitor's alpha-numeric display 20, the user interface buttons 22, and the alarm indicator light 24A. The user interface of FIG. 9 may thus include a native MENU button 22A, a native ENTER button 22B, a native SPOT button 22C and a native CONT. button 22D. Activation of any of these remote device native buttons remotely controls the oxygen monitor 2 to perform the same functions that are performed when the corresponding buttons on the oxygen monitor are pressed.

The native user interface of the remote device 54 may further include a set of native alarm set mode controls 22E that allows a user to remotely control the alarm set mode 60 (see FIG. 6) of the oxygen monitor 2. Although the same functionality may be provided by the native MENU button 22A, the native alarm set mode controls 22E allows a user to control the alarm set mode 60 in a more direct manner.

The alarm set mode controls 22E may include a native TARGET button and associated display element, a native MAX LIMIT button and associated display element, and a native ALARM slide switch element. The native TARGET button and associated display element allows a user to set an ideal % or ppm oxygen value that the user prefers for the weld zone 80 (see FIG. 7). The native MAX LIMIT button and associated display element allows a user to set a maximum % or ppm oxygen value that is allowed in the weld zone 80 during welding. The native ALARM slide switch element allows a user to selectively activate and deactivate oxygen level alarms. When the alarm mode is "ON" (as shown in FIG. 9), the native alpha-numeric display 20 of the touch screen 56 will not only display % and/or ppm oxygen levels, but may also display oxygen level alarms 24A. In FIG. 9, such alarms are generated by changing the background color of the native alpha-numeric display 20. For example, the background color could be (1) red when the oxygen level detected by the oxygen monitor 2 is above the MAX LIMIT oxygen value, (2) yellow when the oxygen level detected by the oxygen monitor 2 is between the MAX LIMIT and TARGET oxygen values, and (3) green when the oxygen level detected by the oxygen monitor 2 is at or below the TARGET oxygen value. FIG. 9 shows the oxygen level at 100 ppm, which would typically produce a green background color if the alarm mode is "ON." A different background color, such as blue, could be displayed in the native alpha-numeric display 20 if the native ALARM slide switch element is set to the alarm "OFF" position. This background color would remain the same regardless of the oxygen level detected by the oxygen monitor 2.

A further native user interface element shown in FIG. 9 is a native CONNECT button 22F. When this button is activated, the remote device 54 establishes wireless communication with the oxygen monitor 2. A suitable visual indicator (such as the indicator light next to the word "CONNECT") may be provided to allow a user to verify that wireless communication has been established. Depending on how the oxygen monitor 2 and the remote device 54 are configured, the ability of the native CONNECT button to selectively establish wireless communication with the oxygen monitor 2 may depend on the oxygen monitor first being placed in its computer mode 66 (see FIG. 6). Alternatively, the oxygen monitor 2 and the remote device 54 could be configured so that the native CONNECT button 22F provides an alternative mechanism for activating the oxygen monitor's computer mode 66.

A further native user interface element shown in FIG. 9 is a native VIEW button 22G. This user interface element allows a user to toggle between the native user interface of FIG. 9 and the mirror user interface of FIG. 7 that emulates some or all of the user interface elements provided on the front side of the oxygen monitor 2.

A further native user interface element shown in FIG. 9 is a native DATA LOGGING slide switch element 22H. This user interface element may be operated by a user to selectively activate and deactivate remote data logging on the remote device 54. Depending on how the oxygen monitor 2 and the remote device 54 are configured, the ability of the DATA LOGGING slide switch element 22F to selectively control remote data logging may depend on the oxygen monitor first being placed in its computer mode 66 (see FIG. 6). Alternatively, the oxygen monitor 2 and the remote device 54 could be configured so that the DATA LOGGING slide switch element 22F provides an alternative mechanism for activating the oxygen monitor's computer mode 66.

Figure 10:
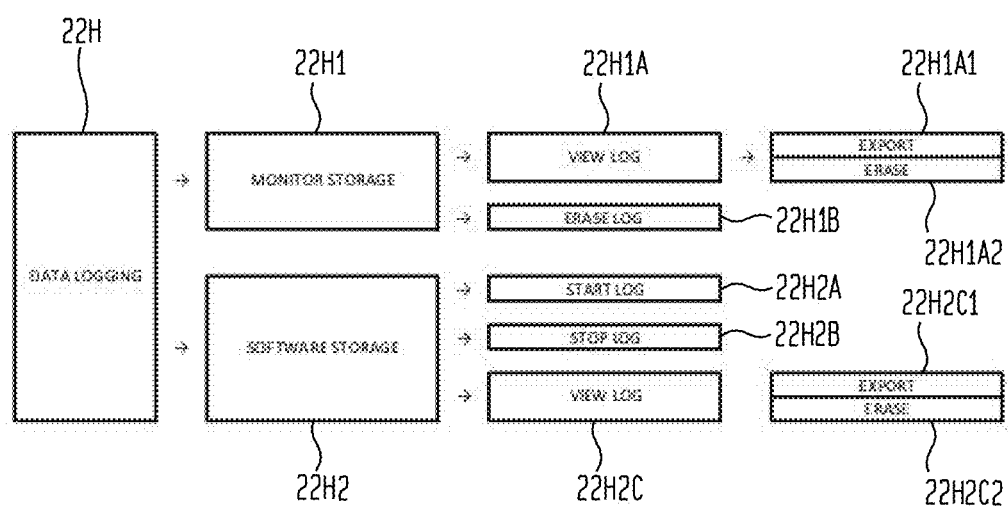
FIG. 10 is a functional block diagram showing data logging user interface operations that may be supported by the alternative user interface of FIG. 9.

With additional reference now to FIG. 10, selection of the native DATA LOGGING slide switch element 22H may activate a sub-menu for selectively managing log data stored in the oxygen monitor storage 46 (see FIG. 5) and/or in the remote device storage 54D. User interface elements associated with these options may include a native MONITOR STORAGE button 22H1 for managing the oxygen monitor's log data and a native SOFTWARE STORAGE button 22H2 for managing the remote device's log data.

Selection of the MONITOR STORAGE option 22H1 may enable two sub-options having associated user interface elements. A first sub-option, which could be invoked by a native VIEW LOG button 22H1A, could allow a user to view the oxygen monitor log data. This sub-option corresponds to the VIEW LOG selection of the SETUP menu 68 shown in FIG. 6. A second sub-option, which could be invoked by a native ERASE LOG button 22H1B, could allow a user to erase all data points and completely erase the log data stored in the oxygen monitor storage 46. This sub-option corresponds to the ERASE LOG selection of the SETUP menu 68 shown in FIG. 6.

Note that selecting the VIEW LOG button 22H1A to invoke oxygen monitor data log viewing may invoke two further sub-options. These two further sub-options may be respectively used to export the oxygen monitor log data and selectively erase a portion of the oxygen monitor log data. The export sub-option, which could be invoked by a native EXPORT button 22H1A1, may result in the log data being sent to a user-selectable destination, such as a directory in the remote device storage 54D, an email address, a cloud storage account, a social media recipient, etc. The erase sub-option, which may be invoked by a native ERASE button 22H1A2, may be used to delete certain data points that are not needed. This sub-option allows a user to reduce the size of the exported data set.

Selection of the SOFTWARE STORAGE option 22H2 may enable three sub-options having associated user interface elements. A first sub-option, which could be invoked by a native START LOG button 22H2A, could allow a user to activate remote data logging to initiate the storing of log data on the remote device 54. A second sub-option, which could be invoked by a native STOP LOG button 22H2B, could allow a user to deactivate remote data logging to discontinue the storing of log data on the remote device 54. A third sub-option, which could be invoked by a VIEW LOG button 22H2C, could allow a user to view log data stored on the remote device 54.

Selecting the VIEW LOG button 22H2C to invoke remote device data log viewing could invoke two further sub-options. These two further sub-options may be respectively used to export the remote device log data and selectively erase a portion of the oxygen monitor log data. The export sub-option, which could be invoked by a native EXPORT button 22H2C1, may result in the log data being sent to a user-selectable destination, such as a directory in the remote device storage 54D, an email address, a cloud storage account, a social media recipient, etc. The erase sub-option, which may be invoked by a native ERASE button 22H2C2, may be used to delete certain data points that are not needed. This sub-option allows a user to reduce the size of the exported data set.

The user interface elements depicted by the remote device display may be generated in any suitable manner. One approach is to use a dedicated application (e.g. cellular telephone "app") running on the remote device 54 that creates its own user interface. This functionality may be provided by the remote device program logic 54I. In such an embodiment, the remote device program logic 54I may be configured to support remote control of the oxygen monitor 2. The oxygen monitor microcontroller 40 may be correspondingly configured to provide an API (Application Program Interface) that enables the remote device 54 to invoke the oxygen monitor's control functions, including some or all of the control functions that a user could invoke via the oxygen monitor's user interface elements 22 (see FIG. 1).

In an alternative embodiment, remote control of the oxygen monitor 2 via the remote device 54 could utilize generic client-server software. For example, the remote device 54 could implement a web browser client that displays a server-generated web page on the remote device display 56. The server-generated user web page could be generated by either the oxygen monitor 2 implementing a generic web server program, or by a separate web server platform (not shown) that intermediates between the oxygen monitor 2 and the remote device 54.

Advantageously, during initial purging of the weld zone and prior to welding, purging personnel do not have to watch the alphanumeric display 20 of the oxygen monitor 2 to determine when the desired oxygen level has been reached. They may leave the weld site to perform other tasks, and check the weld zone oxygen levels via the emulated or native display 20 on the touch screen 56 (or other remote device display). This frees purging personnel from having to remain in close proximity to the weld site, allowing them to engage in other activities while waiting for the weld zone 80 to be purged. As previously noted, the initial purging of a weld zone may take as long as two hours, depending on the size of the weld zone and other factors.

Regardless whether the purging personnel remain at the weld site, both the oxygen monitor 2 and the remote device 54 (if configured as described above) can provide an audio-visual alarm that allows purging personnel to simply listen for an audio alarm to trigger, then optionally glance at a visual alarm indicator, to determine that the weld zone has been purged. If additional assurance is needed, purging personnel may also check the alphanumeric display of either device to confirm the actual oxygen level percentage value for the weld zone 80. Prior to the time that the audiovisual alarm activates, the monitor user may perform other useful functions, such as preparing the welding equipment for the welding operation.

Once welding begins, the remote device may be brought to the weld site and placed in proximity thereto. Alternatively, there may already be a laptop or personal computer at the weld site that the welder may want to use as remote device 54 during welding. Using a laptop or person computer as the remote device during welding has the advantage of providing a large display that allows oxygen data to be easily viewed. During welding, the oxygen monitor 2 will continue to draw gas samples and the welder may periodically monitor either the oxygen monitor's alphanumeric display 20, or its emulated or native counterpart on the remote device 54, in order to verify that the weld zone 80 is being maintained at a suitably low oxygen level. Moreover, the oxygen monitor's audiovisual indicator 24, or its emulated or native counterpart on the remote device 54, may be used to provide audible feedback, such as when the % or ppm oxygen value reaches, or is about to reach, the MAX LIMIT value. In this way, the monitor user will not have to be distracted from the welding task by watching the oxygen monitor's alphanumeric display 20, or its emulated or native counterpart on the remote device 54. The audible warning will apprise the welder of the situation.

When the oxygen monitor's REMOTE MODE of operation is active and the oxygen monitor is wirelessly connected to the remote device 54, the oxygen monitor 2 will wirelessly transmit gas sample data obtained from the gas samples 74 (see FIG. 6) to the remote device. The gas sample data may be transmitted in real time as it is processed by the oxygen monitor's microcontroller 40. The remote device 54 may be programmed to display gas sample oxygen levels via the emulated or native alpha-numeric display 20 (respectively shown in FIGS. 7 and 9), also in real time. If remote DATA LOGGING is enabled on the remote device 54, the remote device may perform remote device logging to log some or all gas of the sample data received from the oxygen monitor 2 in the remote device storage 54D. Such data logging will typically be performed following initial purging at the commencement of the welding operation, and will continue until welding is completed. If desired, gas sample data logging may also be performed prior to welding, during the initial purging operation.

In an embodiment, the remote device 54 may implement gas sample data logging in a manner analogous to, but more robust than, the data logging performed by the oxygen monitor 2. Remote device logging may be implemented automatically, with user control options including viewing log data via the native VIEW LOG button 22H2C or deleting it via the native ERASE button 22H2C2 (see FIG. 10). As also discussed in connection with FIG. 10, the remote device 54 may be configured to allow the oxygen monitor user to remotely enable or disable remote device data logging via the native DATA LOGGING button 22H. Although not shown, the remote device 54 could be additionally enhanced to allow a user to selectively change the rate of logging in order to increase or decrease gas sample data resolution. It would also be possible to provide the ability for a user to selectively disable logging on the oxygen monitor 2 in favor of logging solely on the remote device 54.

The remote device logging event data may include, for each logging event, one or more gas sample oxygen level values obtained during the welding operation by the oxygen monitor 2. The one or more gas sample oxygen levels may be stored in association with timestamps indicating when the gas samples were obtained. The oxygen level values may be stored in raw form, as oxygen level percentage values, as oxygen level ppm values, or any combination of the above. The logging event data may also indicate whether the oxygen monitor's or the remote device's audiovisual alarm 24 was activated at the time of the logging event. For spot oxygen monitoring, there will be a single logging event. For continuous oxygen monitoring, there will be several logging events. By way of example, a logging event could be performed for every "n" gas sample readings, where "n" is selected based on a desired logging event frequency. The logging event frequency "n" may be the same for the remote gas sample logging operation as it is for the oxygen monitor gas sample logging operation. However, the remote device 54 advantageously provides the ability to log gas samples at a much higher frequency than the oxygen monitor 2, without data loss, due to its substantially larger storage capacity.

In the embodiment of FIG. 7, the remote device storage 54D is a cellular telephone storage device whose storage capacity may be as high as 16-64 gigabytes. Other remote device embodiments may have smaller or larger storage capacities. However, most embodiments of the remote device 54 will have a remote storage device many times larger than the oxygen monitor storage 46. As previously noted, the capacity of the oxygen monitor storage 46 may be as small as 1 megabyte. Assuming the size of the remote device storage 54D is in the gigabyte range, such storage will be larger than the oxygen monitor storage 46 by more than factor of 1000:1. This allows the remote device 54 to log significantly more gas sample data than the oxygen monitor 2.

If gas sample readings are taken by the oxygen monitor 2 once per second, the oxygen monitor might perform a logging event every 15 readings, representing a 15 second time span between logging events, in order to conserve storage space. The remote device 54, however, could log more frequently, such as every gas sample reading, to provide much finer logging granularity. This will increase the accuracy of future forensic analysis of the welding operation, if such is needed.

As previously noted, the oxygen monitor storage 46 may only be capable of maintaining a limited first set of gas sample data without overwriting previously written storage locations. The remote device 54, on the other hand, may be capable of simultaneously maintaining at least first and second sets of gas sample data, and likely many thousands of such data sets, without overwriting storage locations. For most weld zone purging applications, the remote device 54 will have virtually unlimited logging capability, allowing extensive purge data gathering to be performed for future forensic use.

Accordingly, a wireless oxygen monitor for monitoring oxygen in a weld zone has been disclosed, together with a distributed oxygen monitor system that includes a wireless oxygen monitor and remote device. A weld zone purging method has also been disclosed. Although various embodiments have been shown and described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A wireless oxygen monitor for monitoring oxygen in a weld zone, comprising:
    a gas inlet port operable to connect said oxygen monitor to a gas sampling probe;
    an electrochemical oxygen sensor operable to receive gas samples from said gas inlet port, detect oxygen in said gas, and generate oxygen sensor outputs indicative of oxygen levels in said gas samples;
    a pump having a pump inlet in fluid communication with said inlet gas port and a pump outlet in fluid communication with said oxygen sensor;
    an oxygen monitor user interface including an oxygen monitor display and one or more user interface buttons;
    an oxygen monitor wireless communication interface;
    an oxygen monitor wired communication interface;
    an oxygen monitor storage; and
    an oxygen monitor controller;
    said oxygen monitor controller being operable to perform oxygen monitor operations, said oxygen monitor operations comprising:
        activating said pump to draw gas samples from said gas inlet port and deliver said samples to said oxygen sensor;
        receiving said oxygen sensor outputs from said oxygen sensor;
        determining oxygen levels of said gas samples from said oxygen sensor outputs;
        displaying gas sample data containing said gas sample oxygen levels on said oxygen monitor display;
        periodically performing oxygen monitor logging to log some but not all of said gas sample data containing said gas sample oxygen levels as logging event data in said oxygen monitor storage;
        responsive to a user input received via said oxygen monitor user interface, selectively implementing (1) a logging event data computer upload mode and (2) a gas sample remote monitoring mode;
        said logging event data computer upload mode comprising transmitting said logging event data to a remote device via one of said oxygen monitor communication interfaces;
        said gas sample remote monitoring mode comprising wirelessly transmitting said gas sample data containing said gas sample oxygen levels via said oxygen monitor wireless communication interface to a remote device that is operable to display said gas sample oxygen levels on a remote device display and to perform remote device logging to log some or all of said gas sample data in a remote device storage;
        said wirelessly transmitting of said gas sample remote monitoring mode being performed in real time for each of said gas samples to allow oxygen monitoring to be performed in real time remotely from said oxygen monitor and said weld zone via said remote device; and
        said wirelessly transmitting of said gas sample remote monitoring mode is performed more often than said oxygen monitor logging in order for said remote device to perform said remote device logging at a higher logging rate than said oxygen monitor logging.

2. The wireless oxygen monitor of claim 1, wherein said oxygen monitor wireless communication interface comprises a wireless network interface.

3. The wireless oxygen monitor of claim 1, wherein said oxygen monitor wireless communication interface comprises a wireless network interface adapted for short range communication within a range up to approximately 30 meters.

4. The wireless oxygen monitor of claim 1, wherein said oxygen monitor wireless communication interface comprises a wireless network interface adapted for short range communication within a range up to approximately 100 meters.

5. The wireless oxygen monitor of claim 1, wherein said wirelessly transmitting of said gas sample remote monitoring mode comprises transmitting said gas sample data to more than one of said remote device.

6. The wireless oxygen monitor of claim 1, wherein said oxygen monitor display displays said gas sample oxygen levels so that a user can monitor said gas sample oxygen levels using either said remote device or said oxygen monitor.

7. The wireless oxygen monitor of claim 1, wherein said operations further include said oxygen monitor receiving control inputs from said remote device via said oxygen monitor wireless communication interface, and said oxygen monitor controller responding to said control inputs to modify one or more operating parameters of said oxygen monitor.

8. The wireless oxygen monitor of claim 1 wherein said oxygen monitor is a portable device, comprising:
    an oxygen monitor housing having a front, a back, a top, a bottom, and two sides extending between said front and back and said top and bottom;

said housing having a hand-holding portion that is sized and configured to be held in the palm of a hand of a monitor user, with the user's thumb engaging one of said sides and the user's remaining fingers engaging the other of said sides; and said oxygen monitor user interface being on said front of said housing.

9. A distributed oxygen monitor system for monitoring oxygen in a weld zone, comprising:
an oxygen monitor for monitoring oxygen in a weld zone, said oxygen monitor comprising:
a gas inlet port operable to connect said oxygen monitor to a gas sampling probe;
an electrochemical oxygen sensor operable to receive gas samples from said gas inlet port, detect oxygen in said gas, and generate oxygen sensor outputs indicative of oxygen levels in said gas samples;
a pump having a pump inlet in fluid communication with said inlet gas port and a pump outlet in fluid communication with said oxygen sensor;
an oxygen monitor user interface including an oxygen monitor display and one or more user interface buttons;
an oxygen monitor wireless communication interface;
an oxygen monitor storage; and
an oxygen monitor controller;
said oxygen monitor controller being operable to perform oxygen monitor operations, said oxygen monitor operations comprising:
activating said pump to draw gas samples from said gas inlet port and deliver said samples to said oxygen sensor;
receiving said oxygen sensor outputs from said oxygen sensor;
determining oxygen levels of said gas samples from said oxygen sensor outputs;
displaying gas sample data containing said gas sample oxygen levels on said oxygen monitor display;
wirelessly transmitting said gas sample data containing said gas sample oxygen levels via said oxygen monitor wireless communication interface to a remote device that is operable to display said gas sample oxygen levels on a remote device display and to perform remote device logging to log said gas sample data in a remote device storage; and
said wirelessly transmitting being performed in real time for each of said gas samples to allow oxygen monitoring to be performed in real time remotely from said oxygen monitor and said weld zone via said remote device;
a remote device operable to wirelessly communicate with said oxygen monitor, said remote device comprising:
a remote device wireless communication interface;
a remote device user interface including a remote device display;
a remote device storage larger than said oxygen monitor storage; and
a remote device controller;
said remote device controller being operable to perform remote device operations, said remote device operations comprising:
wirelessly receiving said gas sample data containing said gas sample oxygen levels for each of said gas samples in real time from said oxygen monitor;
displaying said gas sample data containing said gas sample oxygen levels for each of said gas samples in real time on said remote device display;
performing remote device logging to log some or all of said gas sample data in said remote device storage; and
said oxygen monitor performing oxygen monitor logging to log said gas sample data in said monitor storage, and wherein said remote device logging logs said gas sample data at a higher gas sample logging rate than said oxygen monitor logging.

10. The distributed oxygen monitor system of claim 9, wherein said oxygen monitor wireless communication interface and said remote device wireless communication interface both comprise a wireless network interface.

11. The distributed oxygen monitor system of claim 9, wherein said remote device storage is larger than said oxygen monitor storage by a factor of at least 1000:1.

12. The distributed oxygen monitor of claim 9, wherein there are more than one of said remote device wireless communicating with said oxygen monitor.

13. The distributed oxygen monitor system of claim 9, wherein said remote device is operable to send, and said oxygen monitor is operable to receive, control inputs that modify one or more operating parameters of said oxygen monitor.

14. The distributed oxygen monitor system of claim 9, wherein said remote device is operably responsive to one or more remote device user inputs to selectively control said remote device logging.

15. The distributed oxygen monitor system of claim 9, wherein said remote device display displays said gas sample oxygen levels by selectively mirroring a user interface of said oxygen monitor and providing a native remote device user interface, in response to a user interface selection input received at said remote device user interface.

16. A method for monitoring oxygen in a weld zone established between two pipes to be welded together using an inert gas welding operation, comprising:
providing an oxygen monitor for monitoring oxygen in a weld zone, said oxygen monitor comprising:
a gas inlet port operable to connect said oxygen monitor to a gas sampling probe;
an electrochemical oxygen sensor operable to receive gas samples from said gas inlet port, detect oxygen in said gas, and generate oxygen sensor outputs indicative of oxygen levels in said gas samples;
a pump having a pump inlet in fluid communication with said inlet gas port and a pump outlet in fluid communication with said oxygen sensor;
an oxygen monitor user interface including an oxygen monitor display and one or more user interface buttons;
an oxygen monitor wireless communication interface;
an oxygen monitor storage; and
an oxygen monitor controller;
said oxygen monitor controller being operable to perform oxygen monitor operations, said oxygen monitor operations comprising:
activating said pump to draw gas samples from said gas inlet port and deliver said samples to said oxygen sensor;
receiving said oxygen sensor outputs from said oxygen sensor;
determining oxygen levels of said gas samples from said oxygen sensor outputs;

displaying gas sample data containing said gas sample oxygen levels on said oxygen monitor display;

wirelessly transmitting said gas sample data containing said gas sample oxygen levels via said oxygen monitor wireless communication interface to a remote device that is operable to display said gas sample oxygen levels on a remote device display and to perform remote device logging to log said gas sample data in a remote device storage, said remote device storage being larger than said oxygen monitor storage and capable of simultaneously maintaining at least said first and second sets of said gas sample data without overwriting storage locations; and said wirelessly transmitting being performed in real time for each of said gas samples to allow oxygen monitoring to be performed in real time remotely from said oxygen monitor and said weld zone via said remote device;

providing a remote device operable to wirelessly communicate with said oxygen monitor, said remote device comprising:
  a remote device wireless communication interface;
  a remote device user interface including a remote device display;
  a remote device storage larger than said oxygen monitor storage; and
  a remote device controller;
  said remote device controller being operable to perform remote device operations, said remote device operations comprising:
    wirelessly receiving said gas sample data containing said gas sample oxygen levels for each of said gas samples in real time from said oxygen monitor;
    displaying said gas sample data containing said gas sample oxygen levels for each of said gas samples in real time on said remote device display;
    performing remote device logging to log some or all said gas sample data in said remote device storage; and
    said oxygen monitor performing oxygen monitor logging to log said gas sample data in said oxygen monitor storage, and wherein said remote device logging logs said gas sample data at a higher gas sample logging rate than said oxygen monitor logging;

situating said oxygen monitor proximate to said weld zone;

situating said remote device remote from said oxygen monitor and from said weld zone;

placing said oxygen monitor and said remote device in an operational mode in which said oxygen monitor and said remote device are in wireless communication with each other;

placing said oxygen monitor and said remote device in an operational mode in which said oxygen monitor monitors an oxygen level in said weld zone and said oxygen monitor and said remote device both displays said gas sample oxygen levels;

commencing purging of said weld zone; and monitoring said gas sample oxygen levels remotely from said oxygen monitor and said weld zone via said remote device display or locally at said oxygen monitor and said weld zone via said oxygen monitor display.

17. The method of claim 16, further including, after said gas sample oxygen levels have fallen to a desired value, placing said remote device in an operational mode in which said remote device logging is performed, and commencing an inert gas welding operation.

* * * * *